United States Patent
Terwilliger (10) Patent No.: US 6,931,329 B1
(45) Date of Patent: Aug. 16, 2005

(54) LIKELIHOOD-BASED MODIFICATION OF EXPERIMENTAL CRYSTAL STRUCTURE ELECTRON DENSITY MAPS

(75) Inventor: Thomas C. Terwilliger, Sante Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/512,962

(22) Filed: Feb. 25, 2000

Related U.S. Application Data
(60) Provisional application No. 60/135,252, filed on May 21, 1999.

(51) Int. Cl.[7] .......................... G06F 19/00; G01N 33/48
(52) U.S. Cl. .......................................... 702/27; 702/19
(58) Field of Search ...................... 395/500.23; 702/19, 702/22, 27

(56) References Cited

PUBLICATIONS

Xiang, SB et al., Entropy Maximization constrained by solvent flatness– a new method of for macromolecular phase extension and map improvement; Acta Crystal D–bilogical crystallography; vol. D49 Part 1; (1993); pp. 193–212.*
Drenth, Jan, Principles of Protein X–xay Crystallography; Springer–Velag New York, (1994); pp. 1–19.*
Kevin D. Cowtan et al., "Improvement of Macromolecular Electron–Density Maps by the Simultaneous Application of Real and Reciprocal Space Constraints," International Union of Crystallography, D429, pp. 148–157, 1993.
Bi–Cheng Wang, "Resolution of Phase Ambiguity in Macromolecular Crystallography," Methods in Enzymology, vol. 115, pp. 90–113, 1985.

Shibin Xiang et al., "Entropy Maximization Constrained by Solvent Flatness: a New Method for Macromolecular Phase Extension and Map Improvement," International Union of Crystallography, D49, pp. 193–212, 1993.

G. Bricogne, "Maximum Entropy and the Foundations of Direct Methods," International Union of Crystallography, A40, pp. 410–445, 1984.

G. Bricogne, A Bayesian Statistical Theory of the Phase Problem. 1. A Multichannel Maximum–Entropy Formalism for Constructing Generalized Joint Probability Distribution of Structure Factors, A44, pp. 517–545, (1988).

Thomas C. Terwilliger et al., "Automated MAD and MIR Structure Solution", International Union of Crystallography, D55, pp. 849–861, (1999).

V. Yu. Lunin "Electron–Density Histograms and the Phase Problem," International Union of Crystallography, D49, pp. 90–99, (1993).

* cited by examiner

*Primary Examiner*—Ardin H. Marschel
(74) *Attorney, Agent, or Firm*—Ray G. Wilson (57) ABSTRACT

A maximum-likelihood method for improves an electron density map of an experimental crystal structure. A likelihood of a set of structure factors $\{F_h\}$ is formed for the experimental crystal structure as (1) the likelihood of having obtained an observed set of structure factors $\{F_h^{OBS}\}$ if structure factor set $\{F_h\}$ was correct, and (2) the likelihood that an electron density map resulting from $\{F_h\}$ is consistent with selected prior knowledge about the experimental crystal structure. The set of structure factors $\{F_h\}$ is then adjusted to maximize the likelihood of $\{F_h\}$ for the experimental crystal structure. An improved electron density map is constructed with the maximized structure factors.

5 Claims, 6 Drawing Sheets

LIKELIHOOD-BASED MODIFICATION OF EXPERIMENTAL CRYSTAL STRUCTURE ELECTRON DENSITY MAPS

RELATED APPLICATIONS

This application claims the benefit of U.S. provisional patent application Ser. No. 60/135,252, filed May 21, 1999.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to the determination of crystal structure from the analysis of diffraction patterns, and, more particularly, to macromolecular crystallography.

BACKGROUND OF THE INVENTION

The determination of macromolecular structures, e.g., proteins, by X-ray crystallography is a powerful tool for understanding the arrangement and function of such macromolecules. Very powerful experimental methods exist for determining crystallographic features, e.g., structure factors and phases. While the structure factor amplitudes can be determined quite well, it is frequently necessary to improve or extend the phases before a realistic atomic model of the macromolecule, such as an electron density map, can be built.

Many methods have been developed for improving the phases by modifying initial experimental electron density maps with prior knowledge of characteristics expected in these maps. The fundamental basis of density modification methods is that there are many possible sets of structure factors (amplitudes and phases) that are all reasonably probable based on the limited experimental data that is obtained from a particular experiment, and those structure factors that lead to maps that are most consistent with both the experimental data and the prior knowledge are the most likely overall. In these methods, the choice of prior information that is to be used, and the procedure for combining prior information about electron density with experimentally-derived phase information are important features.

Until recently, electron density modification has generally been carried out in a two-step procedure that is iterated until convergence. In the first step, an electron density map obtained experimentally is modified in real space in order to make it consistent with expectations. The modification can consist of, e.g., flattening solvent regions, averaging non-crystallographic symmetry-related regions, or histogram-matching. In the second step, phases are calculated from the modified map and are combined with the experimental phases to form a new phase set.

The disadvantage of this real-space modification approach is that it is not at all clear how to weight the observed phases from those obtained from the modified map. This is because the modified map contains some of the same information as the original map and some new information. This has been recognized for a long time and a number of approaches have been designed to improve the relative weighting from these two sources, including the use of maximum-entropy methods, the use of weighting optimized using cross-validation, and "solvent-flipping."

A comprehensive theory of the phase problem in X-ray crystallography and a formalism for solving it based on maximum entropy and maximum likelihood methods has been presented by Bricogne, Acta Cryst. A40, pp. 410–445 (1984) and Bricogne, Acta Cryst. A44, pp. 517–545 (1988). This formalism describes the contents of a crystal in terms of a collection of point atoms along with probabilities for their positions. From the positions of these atoms, crystallographic structure factors can be calculated, with a certainty depending on the certainties of the positions of the atoms. Extensions of the formalism are described in Bricogne (1988). The extended formalism specifically addresses the situation encountered in crystals of macromolecules in which defined solvent and macromolecule regions exist in the crystallographic unit cell, and formulas for calculating probabilities of structure factors based on the presence of "flat" solvent regions are presented (Bricogne, 1988). The implementation of this formalism is not straightforward according to Xiang et al., Acta Cryst. D49, pp. 193–212 (1993), who point out that a full fledged implementation of this approach would be highly desirable and would provide a statistical technique for enforcing solvent flatness in advance. Xiang et al (1993) report that they settled for an approximation in which solvent flatness outside the envelope is imposed after the calculation of a model for the distribution of atoms, which corresponds to the existing procedure of flattening the solvent in an electron density map (Wang, Methods Enzymol. 115, pp. 90–112 (1985)).

The present invention solves the same problem that earlier procedures proposed by Bricogne (1988) address, and also includes the use of likelihood as a basis for choosing optimal crystallographic structure factors. The assumptions used in the present procedure differ substantially from those used by Bricogne (1988). For treatment of solvent and macromolecule (protein) regions in a crystal, Bricogne develops statistical relationships among structure factors based on a model of the contents of the crystal in which point atoms are randomly located, but in which atoms in the protein region are sharply-defined with low thermal parameters and atoms in the solvent region are diffuse, with high thermal parameters. In the present approach, no assumptions about the presence of atoms or possible values of thermal factors are used. Instead, it is assumed that values of electron density in the protein and solvent regions, respectively, are distributed in the same way in the crystal as in a model calculation of a crystal that may or may not be composed of discrete atoms.

The methods used to find likely solutions to the phase problem are also very different in the present approach compared to that of Bricogne (1988) because the assumptions used require the problem to be set up in different ways. Bricogne (1988) applies a maximum-entropy formalism developed by Bricogne (1984) to find likely arrangements of atoms in the crystal, which in turn can be used to calculate the arrangement of electron density in the crystal. In the present method, likely values of the structure factors are found by applying a likelihood-based approach based on a combination of experimental information and the likelihood of resulting electron density maps. These structure factors can be used to calculate an electron density map that is then, in turn, a likely arrangement of electron density in the crystal.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, embodied and broadly described herein, the present invention includes a method for improving an electron density map of an experimental crystal structure. A model electron density map of a model crystal structure is formed and model histograms are formed of model electron densities in identified protein and solvent regions of the model electron density map. A model probability distribution function defined by $$p(\rho_T) = \sum_k w_k \exp\left\{-\frac{(\rho - c_k)^2}{2\sigma_k^2}\right\}$$

is fitted to the model histograms, where k is separately indexed over the protein and solvent regions of the model map, $p(\rho_T)$ is a probability of an electron density at a point, $w_k$ is a normalization factor, $\rho$ is electron density, $c_k$ is a mean value of $\rho$, and $\sigma_k$ is a variance of $\rho$, where the fitting determines the coefficients $w_k$, $c_k$, and $\sigma_k$. A set of experimental structure factors is determined from x-ray diffraction data for the experimental crystal structure and forming an experimental electron density map and separate experimental histograms of experimental electron densities are formed over protein and solvent regions of the model electron density map. An experimental probability distribution function defined by $$p(\rho_T) = \sum_k w_k \exp\left\{-\frac{(\rho - \beta c_k)^2}{2(\beta\sigma_k^2 + \sigma_{MAP}^2)}\right\}$$

is fitted to separate protein and solvent regions of the experimental histograms, where $\beta$ is an expectation that an experimental value of $\rho$ is less than a true value and $\sigma_{map}$ is a variance, where the fitting determines the coefficients $\beta$ and $\sigma_{map}$. From the experimental probability distribution function the overall experimental log-likelihood of the electron density in the protein and solvent regions of the experimental map is determined. Then, it is determined how the experimental log-likelihood of the electron density of the protein and solvent regions of the experimental electron density map would change as each experimental structure factor changes to output a revised log-likelihood of any value of each experimental structure factor. Finally, a new set of structure factors is formed from the revised log-likelihood of experimental structure factor values and the new set of structure factors is returned iterate the process until changes to the new set of structure factors is below a predetermined value.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

In accordance with the present invention, experimental phase information is combined with prior knowledge about expected electron density distribution in maps by maximizing a combined likelihood function. The fundamental idea is to express knowledge about the probability of a set of structure factors $\{F_h\}$ ($F_h$ includes amplitude, $F_h$, and phase, $\phi$ factors) and in terms of two quantities: (1) the likelihood of having measured the observed set of structure factors $\{F_h^{OBS}\}$ if this structure factor set $\{F_h\}$ were correct; and (2) the likelihood that the map resulting from this structure factor set $\{F_h\}$ is consistent with prior knowledge about the structure under observation and other macromolecular structures. The index factor h is defined in terms of the hkl plane and unit vectors a*, b*, c* in reciprocal lattice space as h=ha*+kb*+lc.

When formulated in this manner, the overlap of information that occurred in the real-space modification methods is not present because the experimental and prior information are kept separate. Consequently, proper weighting of experimental and prior information only requires estimates of probability functions for each source of information.

The likelihood-based density modification approach has a second very important advantage. This is that the derivatives of the likelihood functions with respect to individual structure factors can be readily calculated in reciprocal space by Fast Fourier Transform (FFT) based methods. As a consequence, density modification simply becomes an optimization of a combined likelihood function by adjustment of structure factors. This makes density modification a remarkably simple but powerful approach, requiring only that suitable likelihood functions be constructed for each aspect of prior knowledge that is to be incorporated.

The basic idea of the likelihood-based density modification procedure is that there are two key kinds of information about the structure factors for a crystal of a macromolecule. The first is the experimental phase and amplitude information, which can be expressed in terms of a likelihood (or a long-likelihood function $LL^{OBS}(F_h)$ for each structure factor $F_h$. The experimental probability distribution for the structure factor, $p^{OBS}(F_h)$ is given by $$p^{OBS}(F_h) = \exp\{LL^{OBS}(F_H)\} \qquad (1)$$

For reflections with accurately-measured amplitudes, the chief uncertainly in $F_h$ will be in the phase, while for unmeasured or poorly-measured reflections, it will be in both phase and amplitude.

The second kind of information about structure factors in this formulation is the likelihood of the map resulting from the factors. For example, for most macromolecular crystals, a set of structure factors $\{F_h\}$ that leads to a map with a flat region corresponding to solvent is more likely to be correct than one that leads to a map with uniform variation everywhere. This map likelihood function describes the probability that the map obtained from a set of structure factors is compatible with expectations:

$$p^{MAP}(F_h) = \exp\{LL^{MAP}(F_H)\} \quad (2)$$

The two principal sources of information are then combined, along with any prior knowledge of the structure factors, to yield the likelihood of a particular set of structure factors:

$$LL(\{F_h\}) = LL^0(\{F_h\}) + LL^{OBS}(\{F_h\}) + LL^{MAP}(\{F_h\}) \quad (3)$$

where $LL^0(\{F_h\})$ includes any structure factor information that is known in advance, such as the distribution of intensities of structure factors.

In order to maximize the overall likelihood function in Eq. (3), the change in the map likelihood function in response to changes in structure factors must be known. In the case of the map likelihood function, $LL^{MAP}(\{F_h\})$, there are two linked relationships: the response of the likelihood function to changes in electron density, and the changes in electron density as a function of changes in structure factors. In principle, the likelihood of a particular map is a complicated function of the electron density over the entire map. Furthermore, the value of any structure factor affects the electron density everywhere in the map.

For simplification, a low-order approximation to the likelihood function for a map is used instead of attempting to evaluate the function precisely. As Fourier transformation is a linear process, each reflection contributes independently to the electron density at a given point in the cell. Although the log-likelihood of the electron density might have any form, it is expected that for sufficiently small changes in structure factors, a first-order approximation to the log-likelihood function would apply and each reflection would also contribute relatively independently to changes in the log-likelihood function.

Consequently, a local approximation to the map likelihood function can be constructed, neglecting correlations among different points in the map and between reflections, expecting that it might describe with reasonable accuracy how the likelihood function would vary in response to small changes in the structure factors. By neglecting correlations among different points in the map, the log-likelihood for the whole electron density map is written as the sum of the log-likelihood of the densities at each point in the map, normalized to the volume of the unit cell and the number of reflections used to construct it:

$$LL^{MAP}(\{F_h\}) \approx \frac{N_{REF}}{V} \int_V LL(x, \{F_h\}) d^3x \quad (4)$$

where $N_{REF}$ is the number of independent reflections and $V$ is the volume.

By treating each reflection as independently contributing to the likelihood function, a local approximation to the log-likelihood of the density at each point $LL(\rho(x,\{F_h^0\}))$ is written. This approximation is given by the sum over all reflections of the first few terms of a Taylor's series expansion around the value obtained with the starting structure factors $\{F_h^0\}$ used in a cycle of density modification, $$LL(\rho(x, \{F_h\})) \approx \quad (5)$$

$$LL(\rho(x, \{F_h^0\})) + \sum_h \left[ \Delta F_{h,\|} \frac{\partial}{\partial F_{h,\|}} LL(\rho(x, \{F_h\})) + \right.$$

-continued $$\frac{1}{2} \Delta F_{h,\|}^2 \frac{\partial^2}{\partial F_{h,\|}^2} LL(\rho(x, \{F_h\})) + \Delta F_{h,\perp} \frac{\partial}{\partial F_{h,\perp}}$$

$$\left. LL(\rho(x, \{F_h\})) + \frac{1}{2} \Delta F_{h,\perp}^2 \frac{\partial^2}{\partial F_{h,\perp}^2} LL(\rho(x, \{F_h\})) + ... \right],$$

where $\Delta F_{h,\|}$ and $\Delta F_{h,\perp}$ are the differences between $F_h$ and $F_h^0$ along the directions $F_h^0$ and $iF_h^0$, respectively.

Combining Eqs. (4) and (5) results in an expression for the map log-likelihood function, $$LL^{MAP}(\{F_h\}) \approx LL^{MAP}(\rho(x, \{F_h^0\})) + \quad (6)$$

$$\frac{N_{REF}}{V} \sum_h \left[ \Delta F_{h,\|} \int_V \frac{\partial}{\partial F_{h,\|}} LL(\rho(x, \{F_h\})) d^3x + \right.$$

$$\frac{1}{2} \Delta F_{h,\|}^2 \int_V \frac{\partial^2}{\partial F_{h,\|}^2} LL(\rho(x, \{F_h\})) d^3x +$$

$$\Delta F_{h,\perp} \int_V \frac{\partial}{\partial F_{h,\perp}} LL(\rho(x, \{F_h\})) d^3x +$$

$$\left. \frac{1}{2} \Delta F_{h,\perp}^2 \int_V \frac{\partial^2}{\partial F_{h,\perp}^2} LL(\rho(x, \{F_h\})) d^3x + ... \right]$$

The integrals in Eq. (6) can be rewritten in a form that is suitable for evaluation by a FFT-based approach. Considering the first integral in Eq. (6), use the chain rule to write, $$\frac{\partial}{\partial F_{h,\|}} LL(\rho(x, \{F_h\})) = \frac{\partial}{\partial \rho(x)} LL(\rho(x, \{F_h\})) \frac{\partial}{\partial F_{h,\|}} \rho(x) \quad (7)$$

and note that the derivative of $\rho(x)$ with respect to $F_{h,\|}$ for a particular index value h is given by, $$\frac{\partial}{\partial F_{h,\|}} \rho(x) = \frac{2}{V} \text{Re}[e^{i\phi_h - 2\pi i h x}] \quad (8)$$

Now the first integral in Eq. (6) is rewritten in the form, $$\int_V \frac{\partial}{\partial F_{h,\|}} LL(\rho(x, \{F_h\})) d^3x = \frac{2}{V} \text{Re}[e^{i\phi_h} a_h^*] \quad (9)$$

where the complex number $a_h$ is a term in the Fourier transform of $$\frac{\partial}{\partial \rho(x)} LL(\rho(x, \{F_h\})), a_h = \int_V \frac{\partial}{\partial \rho(x)} LL(\rho(x, \{F_h\})) e^{2\pi i h x} d^3x \quad (10)$$

in space groups other than P1, only a unique set of structure factors needs to be specified to calculate an electron density map. Taking space group symmetry into account, Eq. (9) can be generalized to read, $$\int_V \frac{\partial}{\partial F_{h,\|}} LL(\rho(x, \{F_h\})) d^3x = \frac{2}{V} \sum_{h'} \text{Re}[e^{i\phi_{h'}} a_{h'}^*] \quad (11)$$

where the indices h' are all indices equivalent to h due to space-group symmetry.

A similar procedure is used to rewrite the second integral in Eq. (6), yielding the expression, $$\int_V \frac{\partial}{\partial F_{h,\parallel}} LL(\rho(x,\{F_h\})) d^3x = \qquad (12)$$

$$\frac{2}{V^2} \sum_{h',k'} Re[e^{i\phi_{h'}} e^{i\phi_{k'}} b_{h'-k'} + e^{-i\phi_{h'}} e^{-i\phi_{k'}} b_{h'+k'}]$$

where the indices h' and k' are each all indices equivalent to h due to space group symmetry, and where the coefficients $b_h$ are again terms in a Fourier transform, this time the second derivative of the log-likelihood of the electron density, $$b_h = \int_V \frac{\partial^2}{\partial^2 \rho(x)^2} LL(\rho(x,\{F_h\})) e^{2\pi i h \cdot x} d^3x \qquad (13)$$

The third and fourth integrals in Eq. (6) can be rewritten in a similar way yielding the expressions, $$\int_V \frac{\partial}{\partial F_{h,\perp}} LL(\rho(x,\{F_h\})) d^3x = \frac{2}{V} \sum_{h'} Re[e^{i\phi_{h'}} a_{h'}^*] \qquad (14)$$

$$\int_V \frac{\partial}{\partial F_{h,\perp}} LL(\rho(x,\{F_h\})) d^3x = \qquad (15)$$

$$\frac{2}{V^2} \sum_{h',k'} Re[e^{-i\phi_{h'}} e^{i\phi_{k'}} b_{h'-k'} - e^{-i\phi_{h'}} e^{-i\phi_{k'}} b_{h'+k'}]$$

The significance of Eqs. (4) through (15) is that there is now a simple expression (Eq. (6)) describing how the map likelihood function $LL^{MAP}(\{F_h\})$ varies when small changes are made in the structure factors. Evaluating this expression requires only that the first and second derivatives of the log-likelihood of the electron density be calculated with respect to electron density at each point in the map (see Eq. (22) below) and that a Fast Fourier Transform (FFT) be carried out as described by Teneyck, Acta Cryst. 33, pp. 486–492 (1977), incorporated by reference. Furthermore, maximization of the (local) overall likelihood function (Eq. (3)) becomes straightforward, as every reflection is treated independently. It consists simply of adjusting each structure factor to maximize its contribution to the approximation to the likelihood function through Eqs. (3)–(15).

In practice, instead of directly maximizing the overall likelihood function, it is used here to estimate the probability distribution for each structure factor, and then to integrate this probability distribution over the phase (or phase and amplitude) of the reflection to obtain a weighted mean estimate of the structure factor. Using Eqs. (3)–(15), the probability distribution for an individual structure factor can be written as, $$\ln p(F_h) \approx LL^0(F_h) + LL^{OBS}(F_h) + \qquad (16)$$

$$\frac{2N_{REF}}{V^2} \Delta F_{h,\parallel} \sum_{h'} Re[e^{i\phi_{h'}} a_{h'}^*] + \frac{2N_{REF}}{V^3} \Delta F_{h,\parallel} 2$$

$$\sum_{h',k'} Re[e^{-i\phi_{h'}} e^{-i\phi_{k'}} b_{h'-k'} + e^{-i\phi_{h'}} e^{-i\phi_{k'}} b_{h'+k'}] +$$

$$\frac{2N_{REF}}{V^2} \Delta F_{h,\perp} \sum_{h'} Re[e^{i\phi_{h'}} a_{h'}^*] + \frac{2N_{REF}}{V^3} \Delta F_{h,\perp} 2$$

$$\sum_{h',k'} Re[e^{-i\phi_{h'}} e^{-i\phi_{k'}} b_{h'-k'} + e^{-i\phi_{h'}} e^{-i\phi_{k'}} b_{h'+k'}]$$

where, as above, the indices h' and k' are each all indices equivalent to h due to space group symmetry, and the coefficients $a_h$ and $b_h$ are given in Eqs. (10) and (13). Also, as before, $\Delta F_{h,\parallel}$ and $\Delta F_{h,\perp}$ are the differences between $F_h$ and $F_h^0$ along the directions $F_h^0$ and $iF_h^0$, respectively. All the quantities in Eq. (16) can be readily calculated once a likelihood function for the electron density and its derivatives are obtained (see Eq. (22) below).

A key step in likelihood-based density modification is the decision as to the likelihood function for values of the electron density at a particular location in the map. For the present purposes, an expression for the log-likelihood of the electron density $LL(\rho(x,\{F_h\}))$ at a particular location x in a map is needed that depends on whether the point satisfies any of a wide variety of conditions, such as being in the protein or solvent region of the crystal, being at a certain location in a known fragment of structure, or being at a certain distance from some other feature of the map. Information can be incorporated on the environment of x by writing the log-likelihood function as the log of the sum of conditional probabilities dependent on the environment of x, $$LL(\rho(x,\{F_h\})) = \ln[p(\rho(x)|PROT)p_{PROT}(x) + p(\rho(x)|SOLV)p_{SOLV}(x)] \qquad (17)$$

where $p_{PROT}(x)$ is the probability that x is in the protein region and $p(\rho(x)|PROT)$ is the conditional probability for $\rho(x)$ given that x is in the protein region, and $p_{SOLV}(x)$ and $p(\rho(x)|SOLV)$ are the corresponding quantities for the solvent region. The probability that x is the protein or solvent region is estimated by a modification, described in Terwilliger, Acta Cryst. D55, pp. 1863–1871 (1999), of the methods described in Wang, Methods Enzymol. 115, pp. 90–112 (1985), and Leslie, Proceedings of the Study Weekend organized by CCP4, pp. 25–32 (1988), incorporated herein by reference. If there were more than just solvent and protein regions that identified the environment of each point, then Eq. (17) could be modified to include those as well.

In developing Eqs. (3)–(15), the derivatives of the likelihood function for electron density were intended to represent how the likelihood function changed when small changes in one structure factor were made. Surprisingly, the likelihood function that is most appropriate for the present invention is not a globally correct one. Instead, it is a likelihood function that represents how the overall likelihood function varies in response to small changes in one structure factor, keeping all others constant. To see the difference, consider the electron density in the solvent region of a macromolecular crystal. In an idealized situation with all possible reflections included, the electron density might be exactly equal to a constant in this region. The goal in using Eq. (16) is to obtain the relative probabilities for each possible value of a particular unknown structure factor $F_h$. If all other structure factors were exact, then the globally correct likelihood function for the electron density (zero unless the solvent region is perfectly flat) would correctly identify the correct value of the unknown structure factor.

Now suppose the phase information is imperfect. The solvent regions would have a significant amount of noise, and the electron density value is no longer a constant. If the globally correct likelihood function is used for the electron density, a zero probability would be assigned to any value of the structure factor that did not lead to an absolutely flat solvent region. This is clearly unreasonable, because all the other (incorrect) structure factors are contributing noise that exists regardless of the value of this structure factor.

This situation is very similar to the one encountered in structure refinement of macromolecular structures where there is a substantial deficiency in the model. The errors in all the other structure factors in the discussion correspond to the deficiency in the macromolecular model in the refinement case. The appropriate variance to use as a weighting factor in refinement includes the estimated model error as well as the error in measurement. Similarly, the appropriate likelihood function for electron density for use in the present method is one in which the overall uncertainty in the electron density due to all reflections other than the one being considered is included in the variance.

A likelihood function of this kind for the electron density can be developed using a model in which the electron density due to all reflections but one is treated as a random variable. See Terwilliger et al., Acta Cryst. D51, pp. 609–618 (1996), incorporated herein by reference. Suppose that the true value of the electron density at x was known and was given by $\rho_T$. Then consider that there are estimates of all the structure factors, but that substantial errors exist in each one. The expected value of the estimate of this electron density ($\rho_{OBS}$) obtained from current estimates of all the structure factors will be given approximately by $<\rho_{OBS}> = \beta\rho_T$, and the expected value of the variance by $<(\rho_{OBS}-\beta\rho_T)^2> = \sigma_{MAP}^2$. The factor $\beta$ represents the expectation that the calculated value of $\rho$ will be smaller than the true value. This is true for two reasons. One is that such an estimate may be calculated using figure-of-merit weighted estimates of structure factors, which will be smaller than the correct ones. The other is that phase error in the structure factors systematically leads to a bias towards a smaller component of the structure factor along the direction of the true structure factor.

A probability function for the electron density at a point x that is appropriate for assessing the probabilities of values of the structure factor for one reflection can now be written as, $$p(\rho) = \exp - \frac{(\rho - \beta\rho_T)^2}{2\sigma_{MAP}^2} \qquad (18)$$

In a slightly more complicated case where the value of $\rho_T$ is not known exactly, but rather has an uncertainly $\sigma_T$, Eq. (18) becomes, $$p(\rho) = \exp - \frac{(\rho - \beta\rho_T)^2}{2(\beta^2\sigma_T^2 + \sigma_{MAP}^2)} \qquad (19)$$

Finally, in the case where only a probability distribution $p(\rho_T)$ for $\rho_T$ is known, Eq. (18) becomes, $$p(\rho) = \int_{\rho_T} p(\rho_T) \exp\left\{-\frac{(\rho - \beta\rho_T)^2}{2\sigma_{MAP}^2}\right\} d\rho_T \qquad (20)$$

Using Eqs. (19) and (20), a histogram-based approach (Goldstein et al., Acta Cryst. D54, pp. 1230–1244 (1998)) can be used to develop likelihood functions for the solvent region of a map and for the macromolecule-containing region of a map. The approach is simple. The probability distribution for true electron density in the solvent or macromolecule regions of a crystal structure is obtained from an analysis of model structures and represented as a sum of gaussian functions of the form, $$p(\rho_T) = \sum_k w_k \exp\left\{-\frac{(\rho - c_k)^2}{2\sigma_k^2}\right\}, \qquad (21)$$

where the coefficients $w_k$ are normalized so that the integral of $p(\rho_T)$ is normalized overall $\rho$.

The coefficients $c_k$, $\sigma_k^2$, and $w_k$ are obtained as follows. A model of a protein structure is used to calculate theoretical structure factors for a crystal of that protein structure. Exemplary structures may be obtained from the Protein Data Bank (H. M. Berman et al., The Protein Data Bank, Nucleic Acids Research 28, pp. 235–242, 2000), and containing space group, cell dimensions and angles, and a list of coordinates, atom types, occupancies, and atomic displacement parameters. The model may be chosen to be similar in size, resolution of the data, and overall atomic displacement factors to the experimental protein structure to be analyzed, but this is not essential to the process. The resolution of the calculated data and the average atomic displacement parameter may be adjusted to match those of the protein structure to be analyzed. Alternatively, a standardized resolution such as 3 Angstrom units and unadjusted atomic displacement parameters may be used, as in the examples given below. The theoretical structure factors for the model are then used to calculate an electron density map.

The electron density map is then divided into "protein" and "solvent" regions in the following way. All points in the map within a specified distance (typically 2.5 Angstrom units) of an atom in the model are designated "protein" and all others are designated "solvent". The next steps are carried out separately for "protein" and "solvent" regions of the electron density map. A histogram of the numbers of points in the protein or solvent region of the electron density map falling into each possible range of electron densities is calculated. The histogram is then normalized so that the sum of all histogram values is equal to unity. Finally, the coefficients $c_k$, $\sigma_k^2$, and $w_k$ are obtained by least-squares fitting of Equation (21) to the normalized histograms. One set of coefficients is obtained for the "protein" region, another for the "solvent" region.

If the values of $\beta$ and $\sigma_{MAP}$ are known for an experimental map with unknown errors, but identified solvent and protein regions, the probability distribution for electron density in each region of the map can be written approximately from Eq. (19) as, $$p(\rho) = \sum_k w_k \exp\left\{-\frac{(\rho - \beta c_k)^2}{2(\beta^2\sigma_k^2 + \sigma_{MAP}^2)}\right\} \qquad (22)$$

with the appropriate values of $\beta$ and $\sigma_{MAP}$ and separate values of $c_k$, $\sigma_k^2$ and $w_k$ for protein and solvent regions. In practice, the values of $\beta$ and $\sigma_{MAP}$ are estimated by a least-squares fitting of the probability distributions for protein and solvent regions given in Eq. (22) to the ones found in the protein and solvent regions in the experimental map.

This fitting is carried out by first constructing separate histograms of values of electron density in the protein and solvent regions defined by the methods described in Wang, Methods Enzymol 115, pp. 90–112 (1985) and Leslie, Proceedings of the Study Weekend, organized by CCP4, pp. 25–32 (1988), incorporated by reference. Next, the histograms are normalized so that the sum, over all values of electron density, of the values in each histogram is unity. In this way the histograms represent the probability that each value of electron density is observed. Then the values of $\beta$ and $\sigma_{MAP}$ in Eq. (22) are adjusted to minimize the squared difference between the values of the probabilities calculated from Eq. (22) and the observed values from the analysis of the histogram. This procedure has the advantage that the scale of the experimental map does not have to be accurately determined. Then Eq. (22) is used with the refined values of β and $\sigma_{MAP}$ as the probability function for electron density in the corresponding region (solvent or macromolecule) of the map.

Figure 1:
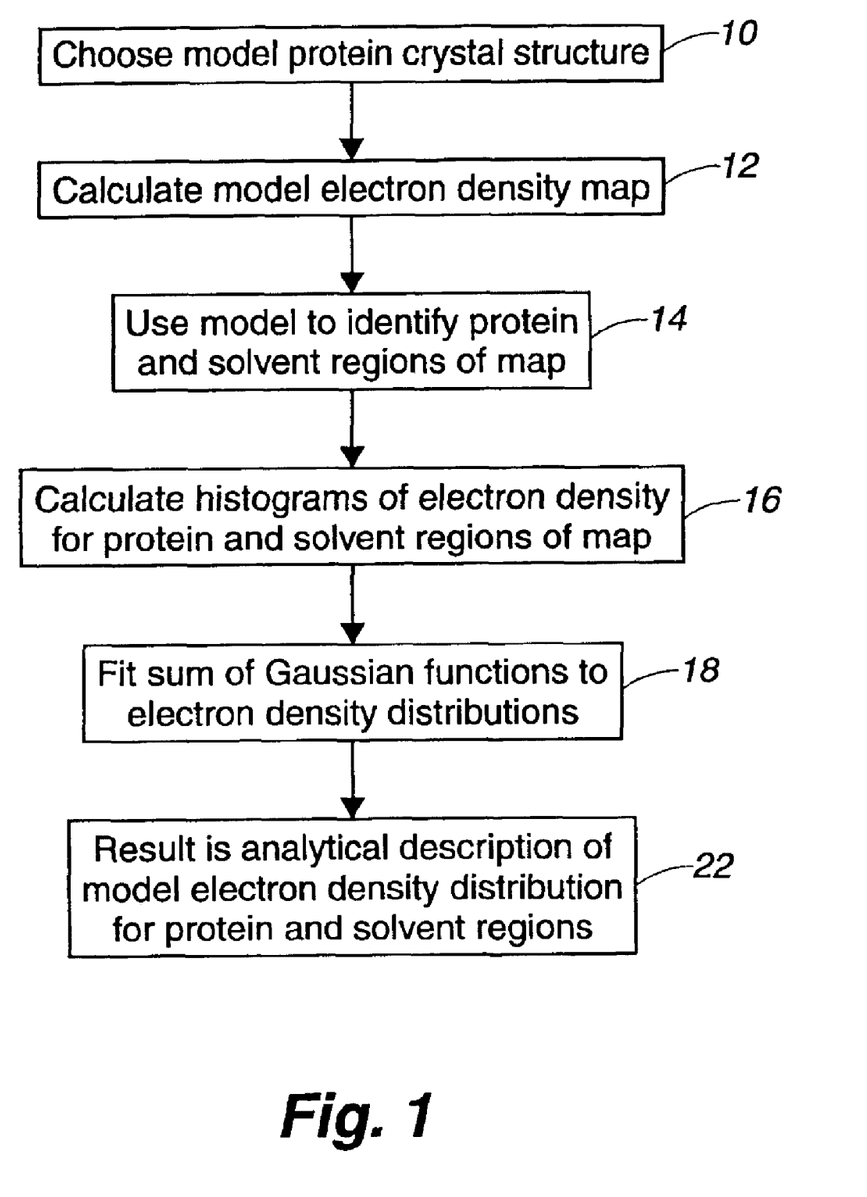
FIG. 1 is a flow sheet for a process to obtain characteristics from a model electron density map.

The process discussed above is more particularly shown in FIGS. 1 and 2. The basic process of maximum-likelihood density modification has two parts. In the first part, the characteristics of model electron density map(s) are obtained (FIG. 1). These will typically be the same or similar for many different applications of the algorithm. In the second part (FIG. 2), a particular set of structure factors has typically been obtained using experimental measurements on a crystal. This set of structure factors can be directly used to calculate an electron density map. Due to uncertainties in measurement, the electron density map is imperfect. In this second part, a set of structure factors (phases and amplitudes) is found that is consistent with experimental measurements of those structure factors, and that, when used to calculate an electron density map, lead to an electron density that has characteristics similar to those obtained from the model electron density map(s). A likelihood-based approach is used to find this optimal set of structure factors.

FIG. 1 shows a process for obtaining characteristics from model electron density maps to use in the above equations. First, a model protein structure obtained by X-ray crystallography is chosen 10. The model is used to conventionally calculate an electron density map 12. The electron density map is segmented into "protein" and "solvent" regions 14, where the protein region contains all points within a selected proximity to an atom in the model. Histograms of electron density are obtained 16 for "protein" and "solvent" regions. For protein and solvent regions, coefficients for the Gaussian function formed by Eq. (21) are found so that Eq. (21) is optimally fitted 18 to the histogram for that region. Eq. (21), with the fitted coefficients, is output 22 as the analytical description of the electron density distribution in the protein or solvent region for this model structure.

Figure 2:
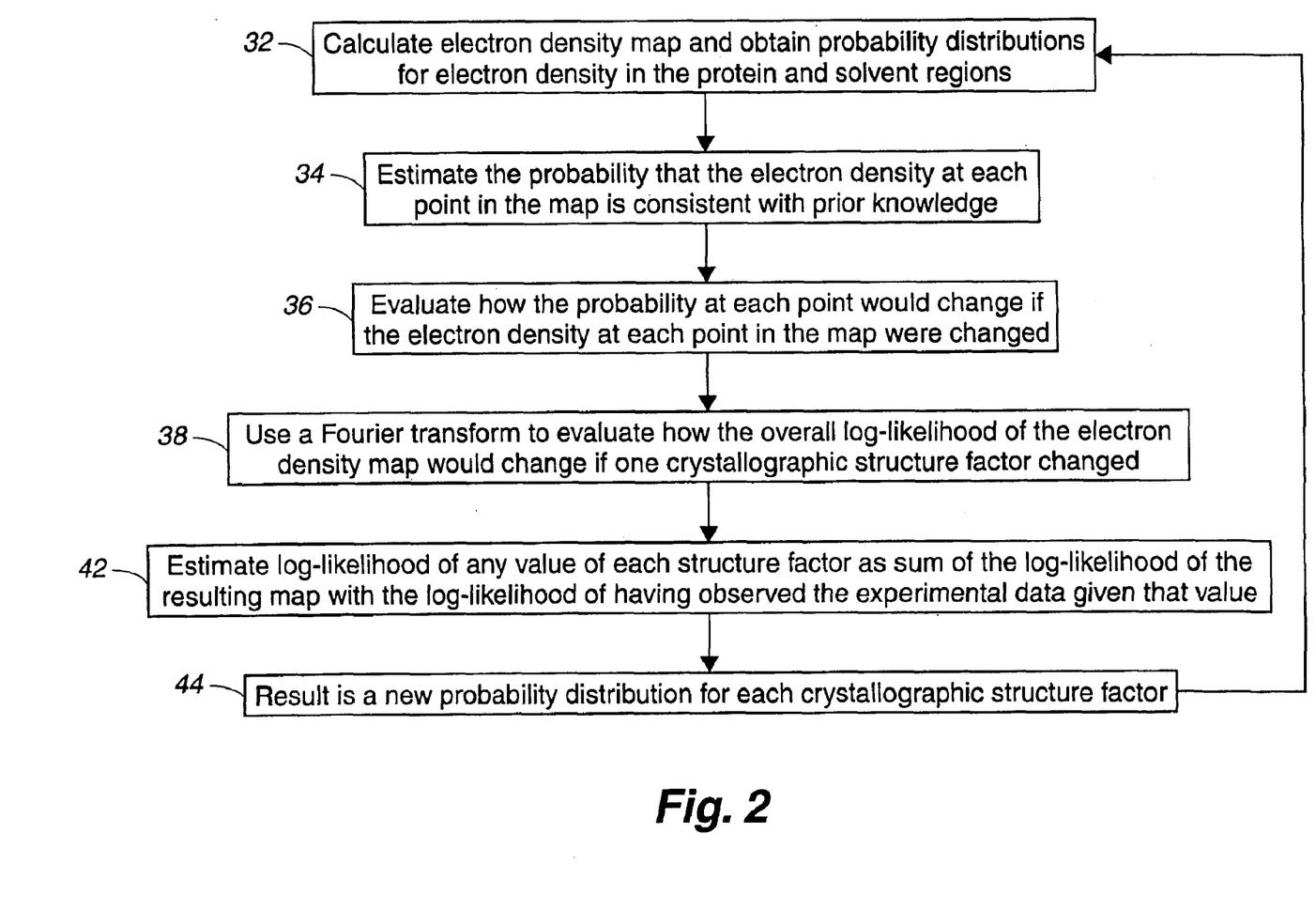
FIG. 2 is a flow sheet for a process to derive structure factors consistent with experimental results which result in an electron density map with expected characteristics.

FIG. 2 depicts the process for finding the optimal set of structure factors for a crystal consistent with experimental measurements and resulting in an the electron density map having characteristics expected from the model structure. The inputs are (1) the analytical descriptions of electron density distributions (Eq. 21) for model solvent and protein regions output from the process shown in FIG. 1; (2) the fraction $f_{solvent}$ of the crystal that is in the "solvent" region; (3) the space group and cell parameters of the crystal; and (4) the experimental measurements of structure factors (phases and amplitudes) and their associated uncertainties.

The overall process steps for estimating the probability that the electron density at each point in the map is correct are: (1) obtaining probability distributions for electron density for the protein and solvent regions of the current electron density map; (2) estimating the probability that the electron density at each point in the map is correct; (3) evaluating how the probabilities would change if the electron density at each point in the map changed; (4) using a Fourier Transform to evaluate how the overall likelihood of the electron density map would change if one crystallographic structure factor changed; (5) combining the likelihood of the map with the likelihood of having observed the experimental data, as a function of each crystallographic structure factor; and (6) deriving a new probability distribution for each crystallographic structure factor. Steps (1) through (6) are then iterated until no substantial further changes in structure factors are obtained.

The process for finding structure factors that are consistent with experiments and that result in an electron density map with expected characteristics is shown in FIG. 2. The current best estimates of structure factors are used to calculate 32 an electron density map. If there is uncertainty in amplitude or phase, the weighted mean structure factor is ordinarily used, where all possible amplitudes and phases are weighted by their relative probabilities. The electron density map is segmented into protein and solvent regions as described by Wang, Methods Enzymol. 115, pp. 90–112 (1985) and Leslie, Proceedings of the Study Weekend organized by CCP4, p. 25–32 (1988), incorporated by reference. The analytical descriptions of electron density distributions for model protein and solvent regions are fitted by least-squares to the observed electron density distributions in the protein and solvent regions in this electron density map using the factors β and $\sigma_{map}^2$, where the same values of β and $\sigma_{map}^2$ are used for both protein and solvent regions.

Eq. (22), with the values of coefficients $c_k$, $\sigma_k$, and $w_k$ for protein and solvent regions obtained from fitting Eq. (21) to the model electron density from the process shown in FIG. 1, and with the values of β and $\sigma_{map}^2$ obtained above, now is an analytical description of a probability distribution for electron density in protein or solvent regions of the electron density map. The derivatives of Eq. (22) with respect to electron density (ρ) are obtained by standard procedures.

The probability of the electron density at each point in the protein or solvent regions of the current map is obtained 34 from Eq. (22). The logarithm of the overall log-likelihood of this map is calculated from the sum of the logarithms of these probabilities. The first and second derivatives with respect to electron density of the probability distributions for each point are calculated 36 to evaluate how the probability at each point would change if the electron density at each point in the map were changed.

An FFT is used to calculate 38, for each structure factor, how the overall log-likelihood of the map would change if that structure factor were changed. Then, the log-likelihood of the map as a function of all possible values of each structure factor is estimated 42 from a Taylor's series expansion of the log-likelihood of the map. This provides a log-likelihood estimate of any value of each structure factor as the sum of the log-likelihood of the resulting map with the log-likelihood of having observed the experimental data given that value.

The new estimate 44 of the logarithm of the probability that a structure factor has a particular value is obtained by adding together the log-likelihood of the map for that value of the structure factor and the log-likelihood of observing the experimental value of the structure factor. The exponentiation of these values is the probability of each possible value of a structure factor and is used to obtain a new weighted estimate of the structure factor. The new estimate of the structure factor is then returned to step 32 to begin a new iteration with a revised electron density map.

To evaluate the utility of maximum-likelihood density modification as described here, the process was applied to both model and real data. The first set of tests consisted of a set of phases constructed from a model with 32%–68% of the volume of the unit cell taken up by protein. The cell was in space group P21212 with cell dimensions of a=94, b=80, c=43 Å and one molecule in the asymmetric unit, and was based on 6906 model data from ∞ to 3.0 Å calculated from coordinates from a dehalogenase enzyme from *Rhodococcus* species ATCC 55388 (ATCC, 1992), except that some of the atoms were not included to vary the fraction of solvent in the unit cell. Phases with simulated errors were generated by adding phase errors to yield an average value of the cosine of the phase error (i.e., the true figure of merit of the phasing) of, $<\cos(\Delta\phi)>=0.42$ for acentric and 0.39 for centric reflections.

Analyses were done using conventional real-space solvent flattening and reciprocal-space solvent flattening, Terwilliger, Acta Cryst. D55, pp. 1863–1871 (1999), incorporated by reference, as well as the maximum-likelihood approach. Both real-space and reciprocal-space solvent flattening improved the quality of phasing considerably. The real space density modification included both solvent flattening and histogram matching to be as comparable as possible to the maximum-likelihood density modification according to the present invention.

Table I shows the quality of phases obtained after each method for density

TABLE I

| Fraction Protein (%) | Starting $<\cos(\Delta\phi)>$ | Real Space $<\cos(\Delta\phi)>$ | Reciprocal Space $<\cos(\Delta\phi)>$ | Maximum Likelihood $<\cos(\Delta\phi)>$ |
|---|---|---|---|---|
| 32 | .41 | .64 | .85 | .87 |
| 42 | .40 | .62 | .67 | .83 |
| 50 | .41 | .54 | .56 | .77 |
| 68 | .42 | .48 | .41 | .53 | modification was applied to this model case. In all cases, maximum-likelihood density modification of this map resulted in phases with an effective figure of merit ($<\cos(\Delta\phi)>$) higher than any of the other methods. When the fraction of solvent in the model unit cell was 50%, for example, maximum-likelihood density modification yielded an effective figure of merit of 0.83, while real-space solvent flattening and histogram matching resulted in an effective figure of merit of 0.62 and reciprocal-space solvent flattening yielded 0.67.

The utility of maximum-likelihood density modification was also compared with real-space density modification and with reciprocal-space solvent flattening using experimental multiwavelength (MAD) data on initiation factor 5A (IF-5A). IF-5A crystallizes in space group I4 with cell dimensions of a=114, b=114, c=33 Å, one molecule in the asymmetric unit, and a solvent content of about 60%. The structure was solved using MAD phasing based on three selenium atoms in the asymmetric unit at a resolution of 2.2 Å. For purposes of testing density modification methods, only one of the three selenium sites was used in phasing here, resulting in a starting map with a correlation coefficient to the map calcuclated using the final refined structure of 0.37.

Figure 3A:
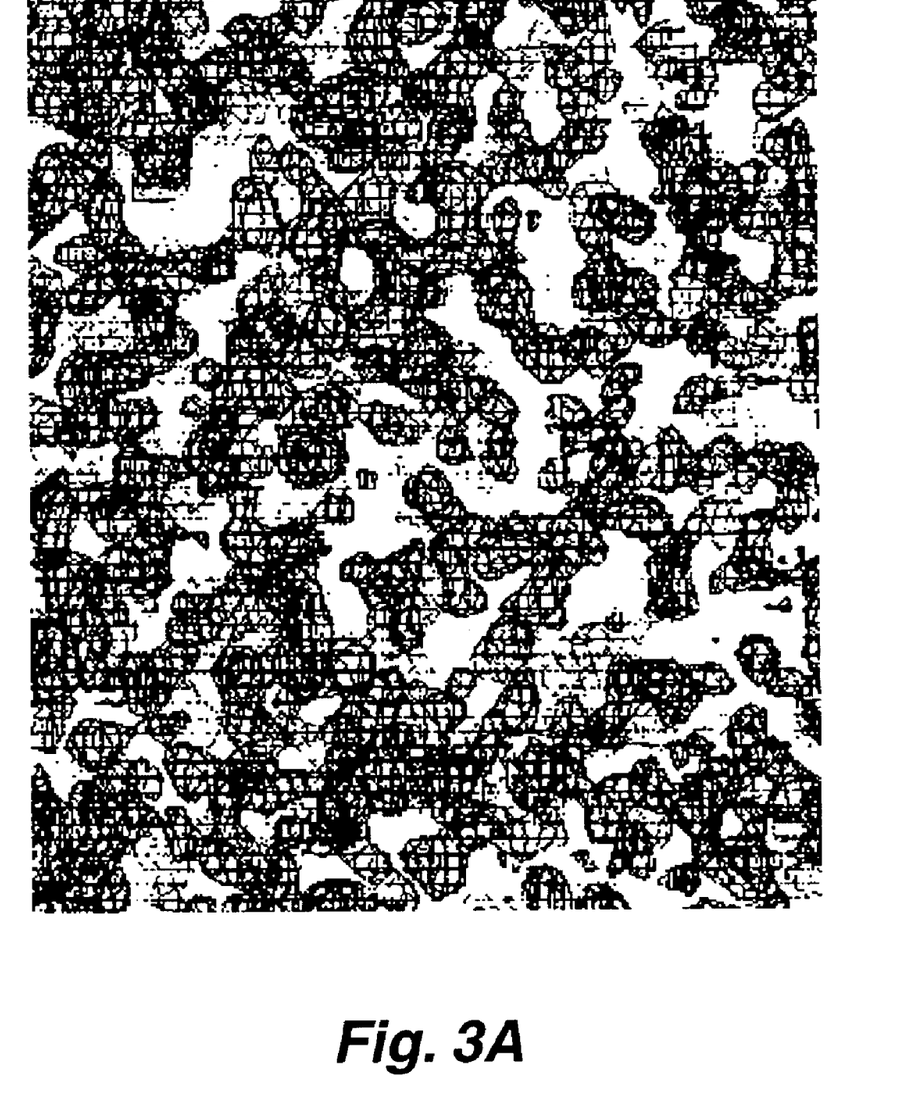
FIG. 3A is a computer-generated electron density map provided by SOLVE software and calculated using only one substituted selenium atom.
Figure 3B:
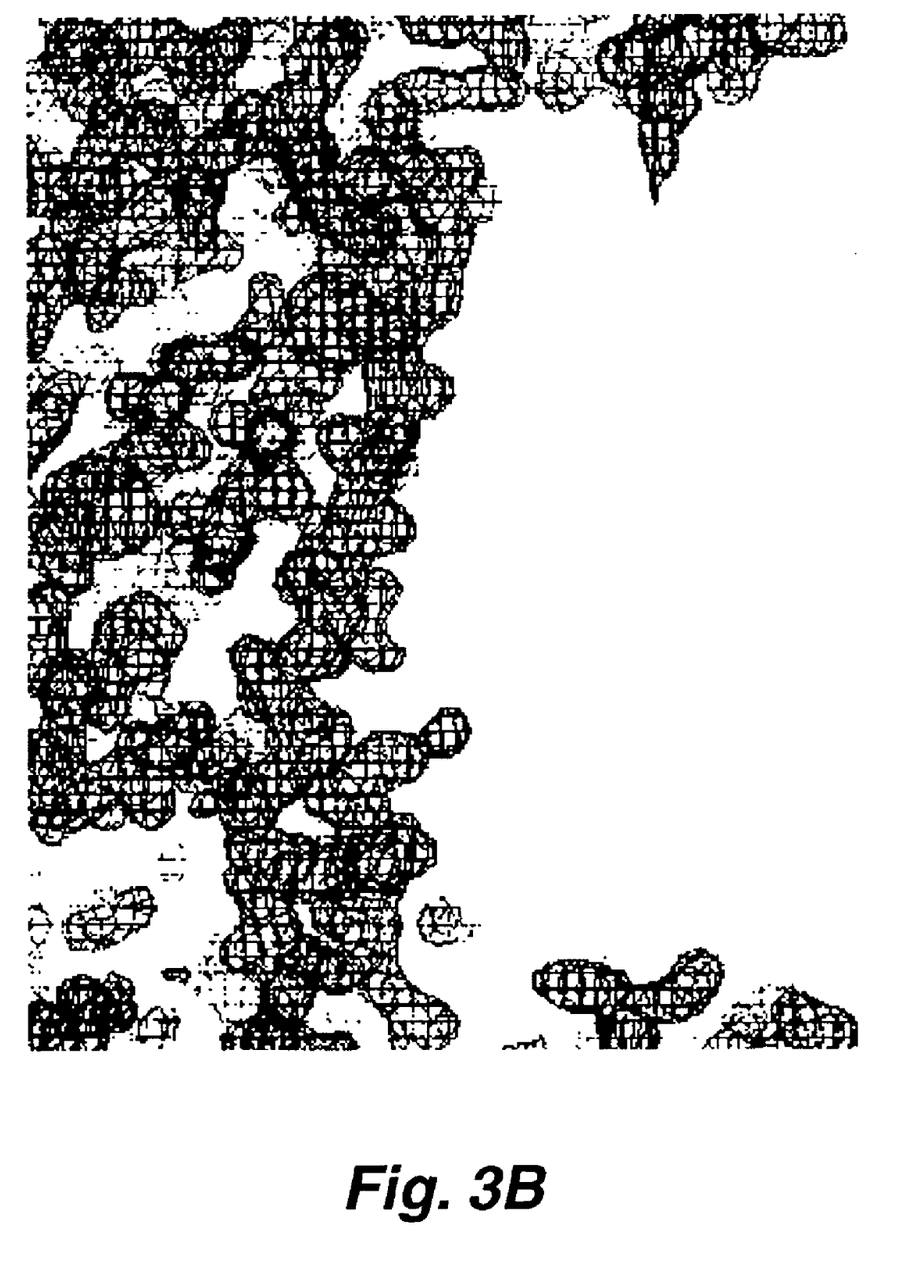
FIG. 3B is a computer-generated model electron density map calculated from an atomic model of the selected protein.
Figure 3C:
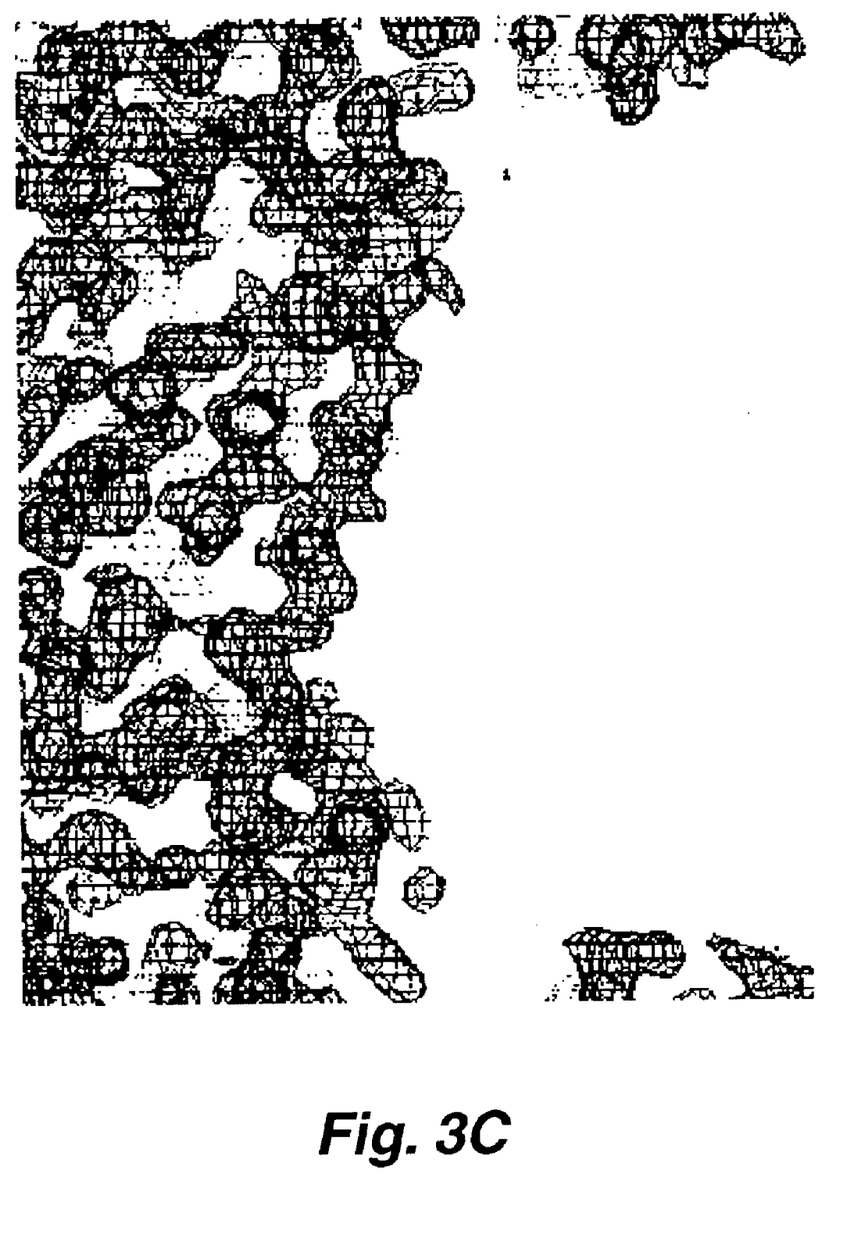
FIG. 3C is a computer-generated electron density map derived from the process shown in FIGS. 1 and 2.
Figure 3D:
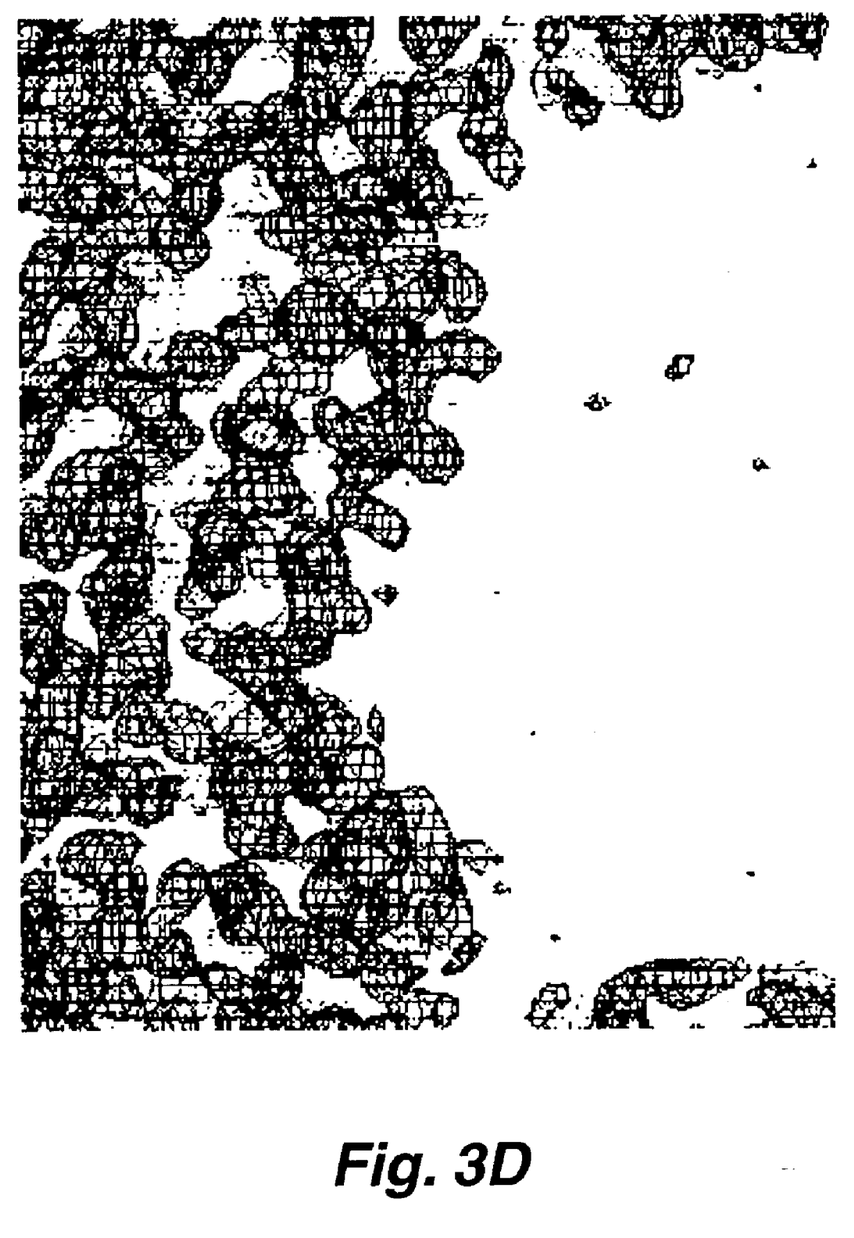
FIG. 3D is a computer-generated electron density map derived from alternate available software called "dm".

FIGS. 3A–D show sections through electron density maps obtained after real-space density modification using solvent flattening and histogram matching and after maximum-liklihood density modification:

FIG. 3A is an electron density map from SOLVE, calculated using only one substituted selenium atom;

FIG. 3B is an electron density map determined from a model structure, calculated from an atomic model of the protein;

FIG. 3C is an electron density map determined using the process of the present invention (RESOLVE);

FIG. 3D is an electron density map calculated using a software program "dm," K. Cowtan, "dm: An automated procedure for phase improvement by density modification," Joint CCP4 and ESF-EACBM Newsletter on Protein Crystallography 31, pp. 34–38 (1994).

As anticipated, the "dm"-modified map is improved over the starting map and has a correlation coefficient of 0.65. The maximum-likelihood modified map is even more substantially improved with a correlation coefficient to the map based on a refined model of 0.79.

While the above demonstration considered only two sources of expected electron density distributions (probability distributions for solvent regions and for protein-containing regions), the methods can be applied directly to a wide variety of sources of information. For example, any source of information about the expected electron density at a particular point in the unit cell that can be written in a form such as the one in Eq. (22) can be used in the procedure to describe the likelihood that a particular value of electron density is consistent with expectation.

Sources of expected electron density information that are especially suitable for application to the present method include non-crystallographic symmetry and the knowledge of the location of fragments of structure in the unit cell. In the case of non-crystallographic symmetry, the probability distribution for electron density at one point in the unit cell can be written using Eq. (22) with a value of $\rho_T$ equal to the weighted mean at all non-crystallographically equivalent points in the cell. The value of $\sigma_T$ can be calculated based on their variances and the value of $\sigma_{MAP}$. In the case of knowledge of locations of fragments in the unit cell, this knowledge can be used to calculate estimates of the electron density distribution for each point in the neighborhood of the fragment. These electron density distributions can then, in turn, be used as described above to estimate $\rho_T$ and $\sigma_T$ in this region.

An iterative process could be developed in which fragment locations are identified by cross-correlation or related searches, density modification is applied, and additional searches are carried out to further generate a model for the electron density. Such a process could potentially even be used to construct a complete probablistic model of a macromolecular structure using structure factor estimates obtained from molecular replacement with fragments of macromolecular structures as a starting point.

In all these cases, the electron density information could be included in much the same way as the probability distributions that are used herein for the solvent and protein regions of maps. In each case, the key is an estimate of the probability distribution for electron density at a point in the map that contains some information that restricts the likely values of electron density at that point. The procedure could be further extended by having probability distributions describing the likelihood that a particular point in the unit cell is within a protein region, within a solvent region, within a particular location in a fragment of protein structure, within a non-crystallographically related region, and so on. These probability distributions could be overlapping or non-overlapping. Then, for each category of points, the probability distribution for electron density within that category could be formulated as in Eq. (22) and the method of the present invention applied.

This process extends reciprocal-space solvent flattening in two important ways. One is that the expected electron density distribution in the non-solvent region is included in the calculations, and a formalism for incorporating information about the electron density map from a wide variety of sources is developed. The second is that the probability distribution for the electron density is calculated using Eq. (22) for both solvent and non-solvent regions and values of the scaling parameter β and the map uncertainty $\sigma_{MAP}$ are estimated by a fitting model and observed electron density distributions. This fitting process makes the whole procedure very robust with respect to scaling of the experimental data, which otherwise would have to be very accurate in order that the model electron density distributions be applicable.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for improving an electron density map of an experimental crystal structure, comprising the steps of:

(a) forming a model electron density map from known crystallographic information of an exemplary model crystal structure;

(b) forming model histograms of model electron densities in identified protein and solvent regions of the model electron density map;

(c) fitting a model probability distribution function defined by $$p(\rho T) = \sum_k w_k \exp\left\{-\frac{(\rho - c_k)^2}{2\sigma_k^2}\right\}$$

to the model histograms, where k is separately indexed over the protein and solvent regions of the model map, $p(\rho_T)$ is a probability of an electron density at a point, $w_k$ is a normalization factor, ρ is electron density, $c_k$ is a mean value of ρ, and $\sigma_k$ is a variance of ρ, where the fitting determines the coefficients $w_k$, $c_k$, and $\sigma_k$;

(d) determining a set of experimental structure factors from x-ray diffraction data for the experimental crystal structure and forming an experimental electron density map;

(e) forming separate experimental histograms of experimental electron densities over protein and solvent regions of the model electron density map;

(f) fitting an experimental probability distribution function defined by $$p(\rho T) = \sum_k w_k \exp\left\{-\frac{(\rho - \beta c_k)^2}{2(\beta\sigma_k^2 + \sigma_{map}^2)}\right\}$$

to separate protein and solvent regions of the experimental histograms, where β is an expectation that an experimental value of ρ is less than a true value and $\sigma_{map}$ is a variance, where the fitting determines the coefficients β and $\sigma_{map}$;

(g) determine the overall experimental log-likelihood of the electron density in the protein and solvent regions of the experimental map from the experimental probability distribution function $$LL(\rho(x,\{F_h\})) = \ln[p(\rho(x)|PROT)p_{PROT}(x) + p(\rho(x)|SOLV)p_{SOLV}(x)]$$

where $p_{PROT}(x)$ is the probability that x is in the protein region and $p(\rho(x)|PROT)$ is the conditional probability for $\rho(x)$ given that x is in the protein region, and $p_{SOLV}(x)$ and $p(\rho(x)|SOLV)$ are the corresponding quantities for the solvent region;

(h) determine how the experimental log-likelihood of the electron density of the protein and solvent regions of the structure factor experimental electron density map would change as each experimental structure factor changes to output a revised log-likelihood of any value of each experimental structure factor;

(i) forming from the revised log-likelihood of experimental structure factor values a new set of structure factors; and (j) forming a revised experimental electron density map from the revised structure factors.

2. The method according to claim 1, wherein step (a) further includes a step of selecting the model crystal structure to be similar in size, data resolution, and atomic displacement factors to the experimental crystal structure.

3. The method according to claim 1, wherein step (b) further includes a step of identifying protein and solvent regions by designating all points within a selected distance of an atom as "protein" and all other points as "solvent".

4. The method according to claim 2, wherein step (b) further includes a step of identifying protein and solvent regions by designating all points within a selected distance of an atom as "protein" and all other points as "solvent".

5. The method according to claim 1, wherein step (h) includes steps of forming a Taylor's series expansion of the log-likelihood of the experimental electron density map and evaluating terms of the Taylor's series expansion using a Fast Fourier Transform.

* * * * *